(12) United States Patent
De Vlaam

(10) Patent No.: US 7,926,664 B2
(45) Date of Patent: Apr. 19, 2011

(54) APPARATUS FOR TRANSFERRING PRODUCTS

(75) Inventor: Hendrikus Louis Stephanus De Vlaam, Almere (NL)

(73) Assignee: FPS Food Processing Systems B.V., Nootdorp (NL)

( * ) Notice: Subject to any disclaimer, the term of this patent is extended or adjusted under 35 U.S.C. 154(b) by 659 days.

(21) Appl. No.: 11/816,596

(22) PCT Filed: Feb. 17, 2006

(86) PCT No.: PCT/NL2006/000084
§ 371 (c)(1),
(2), (4) Date: Apr. 29, 2008

(87) PCT Pub. No.: WO2006/088362
PCT Pub. Date: Aug. 24, 2006

(65) Prior Publication Data
US 2008/0217216 A1 Sep. 11, 2008

(30) Foreign Application Priority Data
Feb. 17, 2005 (EP) .................................. 05075416

(51) Int. Cl.
*A01K 43/04* (2006.01)
(52) U.S. Cl. .................... 209/513; 209/617; 209/903

(58) Field of Classification Search .............. 209/510, 209/513, 514, 656, 698, 617, 903
See application file for complete search history.

(56) References Cited

U.S. PATENT DOCUMENTS

| | | | | |
|---|---|---|---|---|
| 3,278,025 A * | 10/1966 | Willsey et al. | ............. | 209/511 |
| 3,342,012 A | 9/1967 | Reading | | |
| 4,775,051 A | 10/1988 | van der Schoot et al. | | |
| 5,030,001 A * | 7/1991 | vande Vis | ............. | 356/53 |
| 5,277,320 A | 1/1994 | Corkill et al. | | |
| 5,749,453 A | 5/1998 | Doornekamp et al. | | |
| 6,446,784 B1 | 9/2002 | Veldhuizen et al. | | |

* cited by examiner

*Primary Examiner* — Joseph C Rodriguez
(74) *Attorney, Agent, or Firm* — Stites & Harbison PLLC; Marvin Petry

(57) ABSTRACT

An apparatus for transferring products such as eggs from a first conveyor to a second conveyor. During transfer products with certain properties which have been previously detected are allowed to fall into a gap between the conveyors. The transfer uses a rotatable cylinder with radially extending grippers having an open position and a closed position. When a gripper does not grip a product it falls into a gap between the conveyors. Other products are gripped and transferred to the second conveyor. A method for transferring products from a first conveyor to a second conveyor wherein products having certain properties are removed and caused to fall down into a gap between the first and second conveyors. A detected signal upstream from the gap to control positioning of grippers to either transfer products to the second conveyor or allow them to fall into a gap between the two conveyors.

5 Claims, 1 Drawing Sheet

APPARATUS FOR TRANSFERRING PRODUCTS

BACKGROUND OF THE INVENTION

The present invention relates to an apparatus for removing undesirable products, for instance eggs or fruits, from a stream of products, as described in the introductory portion of claim 1.

It is generally known that the chain of food production is to be kept as clean and hygienic as possible. This means that with food processing equipment, measures have to be taken not only for cleaning parts in a simple manner with great regularity but especially also for preventing, from the beginning, any possible pollution. In the present case where products such as eggs or fruit are conveyed and sorted, this has resulted in the development of machines in which, already at the start of the path, undesirable products are removed by the sorting machine so that in the remaining part of the path the pollution is reduced very substantially.

An apparatus as mentioned hereinabove is known from U.S. Pat. No. 4,775,051, also from applicant. After supply of the eggs on an endless roller conveyor on which the eggs, while rotating, are, for instance, inspected for breakage, the eggs are transferred via a transfer element to an endless follow-on conveyor. During transfer, undesirable eggs can be removed, for instance those that have been found unsuitable because of a crack or attached dirt. This removing takes place by temporarily removing the transfer element from the path normally travelled. As a result, the transfer element is given the function of a trapdoor. In the three exemplary embodiments described, as transfer element a trapdoor, wire portion or a flap, respectively, is used. These transfer elements have a substantially fixed position in the continuous stream and are only removed therefrom, in particular folded away or pulled away, when a product has been found undesirable and is to be removed from the apparatus. Further, guides such as a turnstile or a push bar system are used, for guiding the eggs further to the follow-on conveyor as well as for positioning the eggs to be removed to the proper location for removal.

SUMMARY OF THE INVENTION

In order to further improve the above-mentioned system, the apparatus according to the invention is characterized in that the product transfer element takes up the transferring position at least only during transfer of the products from the feed conveyor to and onto the follow-on conveyor, while in the stream of products after the feed conveyor and prior to the follow-on conveyor, the products only come into contact with the product transfer elements.

In contrast with the known apparatus according to U.S. Pat. No. 4,775,051 described hereinabove, where the transfer element, or product transfer element is located virtually permanently in the stream of products, in the feature according to the invention, conversely, the opposite holds true: the product transfer element takes up a product transfer position only with desired and actual transfer. A great advantage thereof is that when this part, or also further parts of the machine, does/do not function properly, the eggs disappear as if by themselves from the stream without causing accumulations, breakage or considerable pollution downstream. Further, with great advantage, the guides also mentioned hereinabove are omitted from the set-up according to the invention so that with them, a source of permanent pollution, soilage and infection is eliminated.

In a further embodiment, the apparatus is characterized in that the apparatus comprises an endless transfer conveyer which is provided with grippers as product transfer elements and which is disposed between the feed conveyor and the follow-on conveyor.

Such an apparatus closely approaches the apparatus according to U.S. Pat. No. 5,749,453, also from applicant. In this publication, a so-called turning apparatus is described with which, with the aid of grippers, eggs are picked up from rollers from an endless feed conveyor, are then, in the turning apparatus, all turned with the point in the same direction and are finally deposited on rollers of a endless follow-on conveyor located downstream. In this manner, all eggs are transferred from the one to the other conveyor. In this document, also, the possibility for removing an undesirable product during transfer is described; however, this takes place only after picking up.

In this embodiment of the apparatus according to the invention, in a highly advantageous manner, an existing machine part is utilized in a different manner while the turning function can still be utilized.

To that end, the apparatus is provided with a control for controlling the product transfer elements designed as grippers, depending on at least one property of a product fed by the feed conveyor and observed by the detector, while normally, the control holds the gripper in an open condition and closes it only when the at least one detected property lies within a predetermined, desired range of criteria. Therefore, normally, the products are removed unless the at least one detected property meets the criteria.

In a following embodiment, the apparatus is characterized in that the endless transfer conveyor is a cylinder drum. Here, advantageously, space and, what is more, equipment parts are economized on.

In a still further embodiment, the apparatus is characterized in that the pitch of the feed conveyor is greater than that of the follow-on conveyor, or, also, in that the pitch of the feed conveyor is smaller than that of the follow-on conveyor.

In the case, for instance, an existing feed conveyor is used, it can be advantageous to increase the pitch downstream to thus be certain that also the larger eggs are processed without breakage on the follow-on conveyor where determination of the egg properties takes place by means of, for instance, optical detection.

In the other case, in particular where for instance the feed conveyor undergoes changes, pitch reduction has as a particular advantage that the gripper half located downstream obtains approximately the same speed as the lay-on roller for the egg to be transferred. In this manner, any damage to a product is suitably prevented.

BRIEF DESCRIPTION OF THE DRAWINGS

Further details of the apparatus according to the invention will be elucidated with reference to a drawing, where the only

DETAILED DESCRIPTION OF PREFERRED EMBODIMENTS

Figure 1:
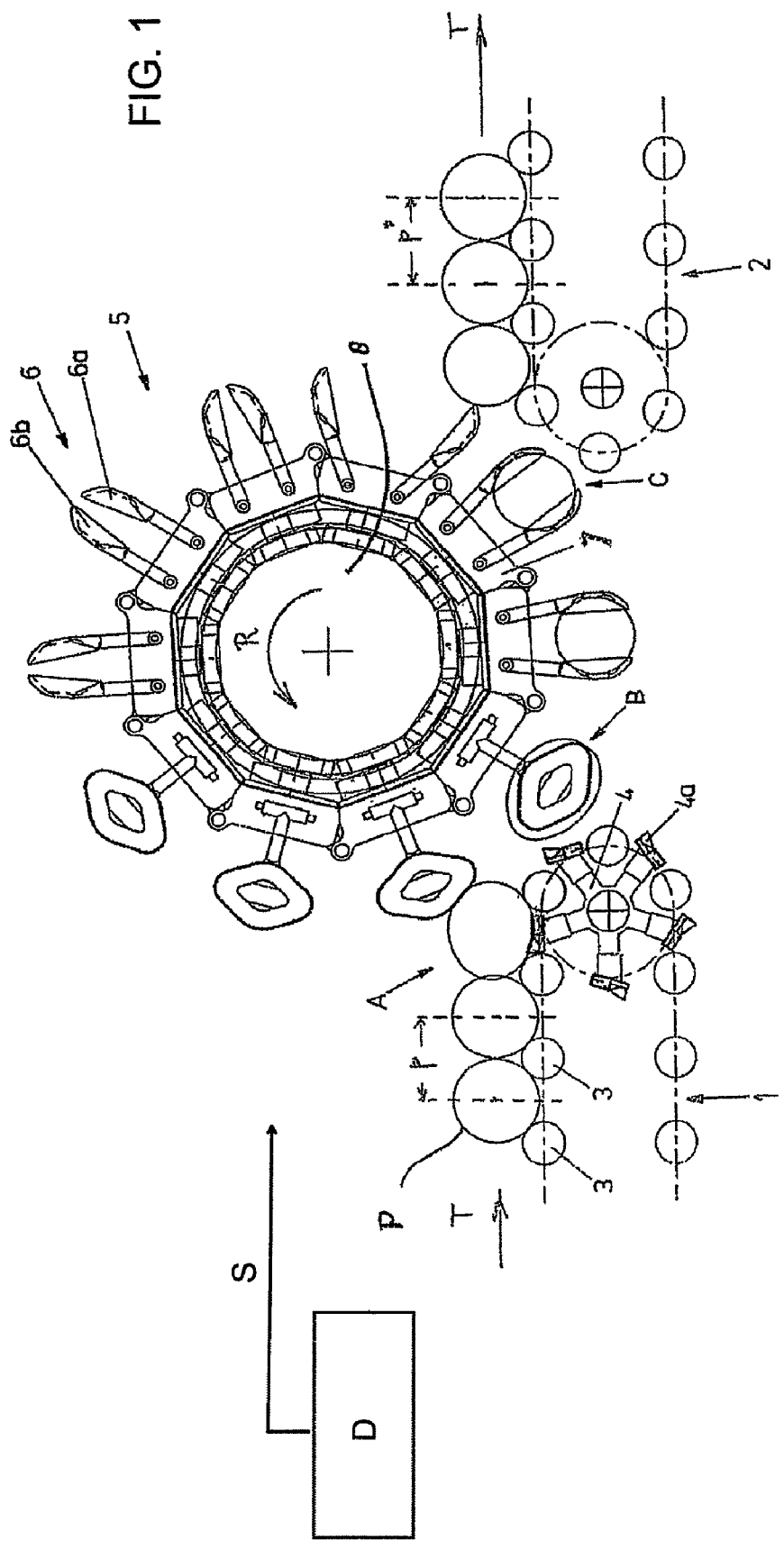
FIG. 1 presents a schematic side view.

In the exemplary embodiment of the invention according to FIG. 1, products P, for instance eggs, are fed in the conveying direction P by an endless feed conveyor 1, are transferred by product transfer elements 6 which are provided on endless transfer conveyor 5, and are then transferred to an endless follow-on conveyor 2.

This feed conveyor 1 is a generally utilized roller conveyor with rollers 3. As a rule, these rollers are hour-glass shaped, i.e. having a constricted center part, with the eggs finding a place, resting on two successive rollers forming part of a row of such successive rollers 3. The distances between the rollers 3, or also the distances, or pitch distances, between the centers between the rollers actually forming the distances between the products P, are for the conveyors 1 and 2, p and p', respectively. In the exemplary embodiment shown, these distances are the same.

Mostly, such a roller conveyor comprises several rows side by side. In the arrangement of a sorting system for eggs, the roller conveyor has the function of feeding the eggs in a sorted manner suitable to the sorting system, after the eggs have been picked up by a system of suction cup elements from, for instance, trays and have been deposited on the rollers.

In the exemplary embodiment represented, the transfer conveyor 5 is a cylinder drum 8 with an endless chain to which the product transfer elements 6 are connected. More particularly, the chain consists of links or segments 7 to which the product transfer elements are connected while the elements used are grippers 6 with grippers hands 6a, b. By means of these grippers, the products are picked up from conveyor 1, carried along by the drum 8 rotating in direction of rotation R, and thereupon, deposited once more on the conveyor. Opening and closing of such grippers is known from, for instance, earlier cited U.S. Pat. No. 5,749,453, wherein a combination of a cam and cam track is utilized. With this, the paths over which the grippers 6 are opened or closed are defined. It is further possible to provide a combination of paths so that, also, the status of a path can be changed, for instance from opened to closed or the reverse, arranged by cam switches specially provided thereto. For the use according to the present invention, this means that when an undesirable product, for instance a leaking egg, is supplied, the cam track is controlled by cam switches in a manner such, by, for instance, a signal S produced by a detector D having detected this situation, that the grippers remain open and the egg is not picked up. Upon arrival at the downstream end of the feed conveyor 1, this egg will fall down from the rollers 3 and thus be removed from the stream of eggs. Then, during the following rotation, or cycle, such a gripper will be restored to a position wherein once more, with a cam switch, a choice can be made. What is thus achieved is that in an optimal manner the grippers are only closed upon actual transfer. In this way, for any other situation, in particular in case of malfunctions, the grippers can be positioned such that feed-through and transfer of eggs is avoided, thereby preventing any possible pollution by undesirable products.

It is further indicated in the FIGURE that the grippers can rotate, also described in detail in U.S. Pat. No. 5,749,453, in which the eggs are brought in a pre-oriented position A by pre-orienting elements 4 while after transfer, the eggs are brought in an intermediate position B, and finally, upon depositing, the eggs are brought in an aligned position C. With this, it becomes clear that for the existing set-up the use is optimized such that, upon transfer, in addition to orienting, the removal of the products found undesirable can take place.

In addition to the above-mentioned functions, the function of ejecting eggs during transfer with the cylinder drum can be applied in combination with the already described functions, more particularly for eggs that are, for instance, damaged or soiled to a limited extent. In case of such a special selection, the eggs can be discharged in a known manner. When soiled to a limited extent, eggs can still be led through a washing system or, also, to a sorting belt intended thereto. Likewise, slightly damaged eggs can be removed and be ranged in special selections.

In a further exemplary embodiment, for instance as desired by a user, a set-up and combination of cam and cam track can be opted for, where the grippers are also closed with empty feed positions, or where all eggs are transferred especially in the case of malfunction. What is prevented in the latter case is that too many eggs are removed from the stream.

For further use of preventing transfer of undesirable products, one or several grippers connected to and moved by a robot arm can be considered. This may for instance the case when sorting and packaging large fruits such as melons.

It will be clear to any person skilled in the art that minor modifications are understood to fall within the scope of protection of the annexed claims.

The invention claimed is:

1. A method for transferring products from a first conveyor to a second conveyor which includes selecting and removing those products having a certain property, comprising the steps of:
    moving the products along a first conveyor and then along a second conveyor located downstream from the first conveyor to form a gap between the two conveyors,
    transferring the products from the first conveyor to the second conveyor using grippers having a closed gripping position and an open release position,
    detecting a given property of each product upstream from the gap and sending a signal to the grippers relating to whether a given product associated with that gripper has the certain property, such that for products having that property, the grippers take up the open release position so as to not grip those products while on the first conveyor, allowing those products to fall into the gap between the two conveyors and not be transferred to the second conveyor and for products which do not have the certain property, the grippers take up the closed gripping position to grip those products while on the first conveyor to transfer those products from the first conveyor to the second conveyor.

2. The method of claim 1, wherein the products are eggs and the detecting step detects an undesirable property of the eggs, and when the grippers take up an open position related to an egg having an undesirable property, that egg is then permitted to fall into the gap between the conveyors.

3. The method of claim 1, wherein moving the products along the first conveyor comprises moving them on rollers of a roller conveyor and moving the products along the second conveyor comprises moving them along rollers of a roller conveyor wherein the two conveyors are in essentially the same horizontal plane and the rollers of the second conveyor are aligned with the rollers of the first conveyor.

4. The method according to claim 1, wherein the transferring step includes transferring the eggs with a cylindrical transfer device comprising a cylinder which is rotatable about an axis perpendicular to the direction of movement of the two conveyors, and with grippers extending radially outwardly from the cylinder of the transfer device.

5. The method according to claim 1, wherein the step of gripping the products with grippers includes rotating the grippers about their own axes so as to reorient products being transferred from the first conveyor to the second conveyor.

* * * * *